(12) United States Patent
Mokelke et al.

(10) Patent No.: US 9,403,007 B2
(45) Date of Patent: Aug. 2, 2016

(54) SYSTEMS AND METHODS TO REDUCE SYNCOPE RISK DURING NEURAL STIMULATION THERAPY

(71) Applicant: Cardiac Pacemakers, Inc., St. Paul, MN (US)

(72) Inventors: Eric A. Mokelke, White Bear Lake, MN (US); Shibaji Shome, Arden Hills, MN (US); Guy Alvarez, Lino Lakes, MN (US); Harlan Bos, Stillwater, MN (US); Kenneth Martin Stein, Minneapolis, MN (US); John D. Hatlestad, Maplewood, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 336 days.

(21) Appl. No.: 13/894,348

(22) Filed: May 14, 2013

(65) Prior Publication Data

US 2013/0338727 A1  Dec. 19, 2013

Related U.S. Application Data

(60) Provisional application No. 61/659,753, filed on Jun. 14, 2012.

(51) Int. Cl.
*A61N 1/36* (2006.01)
*A61B 5/11* (2006.01)
*A61B 5/00* (2006.01)

(52) U.S. Cl.
CPC ............ *A61N 1/3606* (2013.01); *A61B 5/1116* (2013.01); *A61N 1/3615* (2013.01); *A61N 1/36139* (2013.01); *A61N 1/36167* (2013.01); *A61B 5/1118* (2013.01); *A61B 5/4836* (2013.01); *A61B 5/686* (2013.01); *A61B 2560/0209* (2013.01); *A61N 1/36117* (2013.01)

(58) Field of Classification Search
CPC ........... A61N 1/36139; A61N 1/36135; A61N 1/36114; A61N 1/3606; A61N 1/36117; A61B 5/1116; A61B 5/1118
See application file for complete search history.

(56) References Cited

U.S. PATENT DOCUMENTS

| | | | |
|---|---|---|---|
| 7,643,875 B2 | 1/2010 | Hiel, Jr. et al. | |
| 7,706,884 B2 | 4/2010 | Libbus | |
| 7,747,323 B2 | 6/2010 | Libbus et al. | |
| 7,869,881 B2 | 1/2011 | Libbus et al. | |
| 8,676,326 B1* | 3/2014 | Farazi | 607/44 |
| 2007/0249968 A1* | 10/2007 | Miesel et al. | 600/595 |
| 2007/0260285 A1 | 11/2007 | Libbus et al. | |
| 2008/0021504 A1 | 1/2008 | McCabe et al. | |
| 2008/0051839 A1 | 2/2008 | Libbus et al. | |
| 2008/0082001 A1* | 4/2008 | Hatlestad et al. | 600/481 |
| 2008/0082137 A1 | 4/2008 | Kieval et al. | |
| 2008/0171923 A1 | 7/2008 | Bolea et al. | |
| 2008/0177350 A1 | 7/2008 | Kieval et al. | |
| 2008/0234780 A1 | 9/2008 | Smith et al. | |

(Continued)

*Primary Examiner* — Michael Kahelin
(74) *Attorney, Agent, or Firm* — Schwegman Lundberg & Woessner, P.A.

(57) ABSTRACT

Some embodiments, by way of example, provide a system, comprising a posture change detector configured to detect a posture transition indicative of an increased risk of syncope, and a neural stimulator configured to deliver a neural stimulation therapy. The neural stimulator may include a syncope avoidance module configured to respond to a detected posture transition by temporarily overriding the neural stimulation therapy to ameliorate the risk of increased syncope.

20 Claims, 8 Drawing Sheets

(56) References Cited

U.S. PATENT DOCUMENTS

| | | |
|---|---|---|
| 2009/0030478 A1 | 1/2009 | Kieval et al. |
| 2009/0132002 A1 | 5/2009 | Kieval |
| 2010/0076511 A1 | 3/2010 | Heil, Jr. et al. |
| 2010/0121399 A1 | 5/2010 | McCabe et al. |

* cited by examiner

SYSTEMS AND METHODS TO REDUCE SYNCOPE RISK DURING NEURAL STIMULATION THERAPY

CLAIM OF PRIORITY

This application claims the benefit of U.S. Provisional Application No. 61/659,753, filed on Jun. 14, 2012, under 35 U.S.C. §119(e), which is hereby incorporated by reference in its entirety.

TECHNICAL FIELD

This application relates generally to medical devices and, more particularly, to systems, devices and methods to reduce syncope risk during neural stimulation therapy.

BACKGROUND

Therapies that are based on autonomic modulation have shown efficacy in a variety of diseases, including cardiovascular diseases, in both preclinical and clinical studies. The autonomic balance can be modulated to have more parasympathetic tone by stimulating nerve traffic in parasympathetic targets or inhibiting nerve traffic in sympathetic targets, and can be modulated to have more sympathetic tone by stimulating nerve traffic in sympathetic targets or inhibiting nerve traffic in parasympathetic targets.

Sympathetic overactivation is involved in a variety of cardiovascular disease, such as ventricular arrhythmias, myocardial infarction (MI), heart failure (HF), etc. For example, vagus nerve stimulation, which generally increases parasympathetic tone, has been proposed as a therapy for cardiovascular problems such as cardiac rhythm management, myocardial infarction and ischemia, heart failure (HF), hypertension, and sleep disordered breathing. Further, by way of example, vagal stimulation also has been proposed as a therapy for epilepsy, depression, pain, migraines, eating disorders/obesity, and movement disorders. Stimulation of other neural targets has been proposed. For example, stimulation of baroreceptor regions or the carotid sinus nerve has been proposed to treat hypertension, deep brain stimulation has been proposed to treat depression and dementia, and spinal cord stimulation has been proposed to treat pain.

SUMMARY

Some embodiments, by way of example, provide a system, comprising a posture change detector configured to detect a posture transition indicative of an increased risk of syncope, and a neural stimulator configured to deliver a neural stimulation therapy. The neural stimulator may include a syncope avoidance module configured to respond to a detected posture transition by temporarily overriding the neural stimulation therapy to ameliorate the risk of increased syncope.

Some embodiments, by way of example, provide a method, comprising delivering a neural stimulation therapy, detecting a posture transition indicative of an increased risk of syncope, and temporarily overriding the neural stimulation therapy in response to detecting the posture transition to ameliorate the risk of increased syncope.

Some embodiments, by way of example, provide a posture monitor configured to monitor posture of a patient, comprising an activity sensor an activity sensor configured to sense patient activity and a posture sensor configured to sense patient posture. The posture monitor may include an activity sampler configured to control the activity sensor to sample patient activity and detect an increase in patient activity, and a posture sampler configured to control the posture sensor, in response to a detected increase in patient activity, to sample patient posture.

Some embodiments, by way of example, provide a method for monitoring patient posture, comprising sampling patient activity using an activity sensor configured to sense patient activity and detect an increase in patient activity, and sampling patient posture in response to a detected increase in patient activity using a posture sensor configured to sense patient posture.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
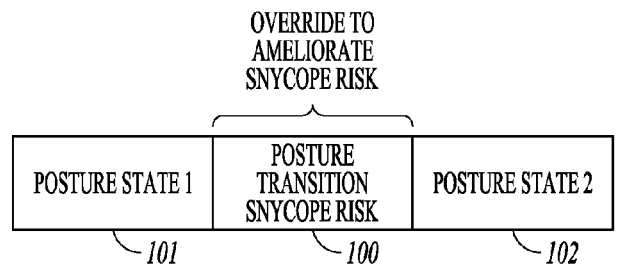
FIG. 1 illustrates a transition between posture states indicative of a risk of syncope, and the therapy override to ameliorate the risk of syncope according to an example of the present subject matter.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The autonomic nervous system (ANS) regulates "involuntary" organs (in contrast to the somatic nervous system, responsible for volitional body system control e.g., the contraction of skeletal muscles). Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS is divided into the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and can work in concert with the somatic nervous system.

The ANS has direct influences on cardiac performance. The heart rate and contractility are increased when the sympathetic nervous system is stimulated, and are decreased when the sympathetic nervous system is inhibited (or the parasympathetic nervous system is stimulated).

Stimulating the sympathetic and parasympathetic nervous systems can have effects other than heart rate and blood pressure. For example, stimulating the sympathetic nervous system, depending upon the site of stimulation, can dilate the pupil, reduce saliva and mucus production, relax the bronchial muscle, reduce the successive waves of involuntary contraction (peristalsis) of the stomach and the motility of the stomach, increase the conversion of glycogen to glucose by the liver, decrease urine secretion by the kidneys, and relax the wall and closes the sphincter of the bladder. Stimulating the parasympathetic nervous system has different and typically opposite effects to stimulation of the sympathetic nervous system: constriction of the pupil, increased saliva and mucus production, contraction of the bronchial muscle, increased secretions and motility in the stomach and large intestine, increased digestion in the small intestine, increased urine secretion, and contraction the wall and relaxation of the sphincter of the bladder. The functions associated with the sympathetic and parasympathetic nervous systems are many and can be complexly integrated with each other.

A pressoreceptive region or field is capable of sensing changes in pressure, such as changes in blood pressure. A baroreceptor generally senses pressure changes. Baroreceptors function as the receptor of a central reflex mechanism that tends to reduce the pressure. The baroreflex is the reflex response triggered by baroreceptors. Baroreflex functions as a negative feedback system. Increased pressure stretches blood vessels, which in turn activates baroreceptors in the vessel walls. Activation of baroreceptors naturally occurs through internal pressure and stretching of the arterial wall, causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance. The baroreflex can be stimulated by stimulating afferent nerves or sensory nerve endings that are sensitive to the stretching of the vessel wall that results from increased blood pressure from within.

Afferent nerve trunks leading from baroreceptors have been stimulated to induce a baroreflex response. For example, direct electrical stimulation has been applied to the vagal nerve and carotid sinus. Research has indicated that electrical stimulation of the carotid sinus nerve can result in reduction of experimental hypertension, and that direct electrical stimulation to the pressoreceptive regions of the carotid sinus itself brings about reflex reduction in experimental hypertension.

Neural stimulation may be used to treat a variety of disorders, including but not limited to cardiovascular disorders such as hypertension and heart failure. These conditions are briefly described below. Hypertension is a cause of heart disease and other related cardiac co-morbidities. Hypertension occurs when blood vessels constrict. As a result, the heart works harder to maintain flow at a higher blood pressure, which can result in compensatory cardiac remodeling, which often contributes to heart failure. Hypertension generally relates to high blood pressure, such as a transitory or sustained elevation of systemic arterial blood pressure to a level that is likely to induce cardiovascular damage or other adverse consequences. Hypertension may be defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease. Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Baroreflex stimulation, also referred to as barostimulation, has been shown to cause immediate reductions in blood pressure (BP) and heart rate (HR). Conversely, when barostimulation is turned OFF, the return of BP/HR to pre-activation levels is also rapid. Changes in posture (e.g. changing from sitting to standing) can result in marked transient reductions in BP/HR. This change in posture is naturally counteracted by baroreflex activity, which provides a reflex response to the transient reduction in BP/HR by increasing sympathetic tone and raising BP/HR to normalized levels. Syncope refers to fainting, and is caused by diminished cerebral blood flow that often results from hypotension. A type of syncope is postural syncope, which may occur upon assuming a more upright position. A healthy baroreflex response quickly raises blood pressure by constricting blood vessels and raising heart rate. Postural syncope may be caused by an under-responsive baroreflex. For example, the baroreflex of some patients such as the elderly and/or people taking certain medications may provide inadequate neural control of blood pressure, which may result in syncope upon rising from a sitting position or other sudden posture changes. A patient may experience pre-syncope symptoms, such as lightheadedness, nausea, abnormal perspiration, weakness, dizziness, changes in vision and/or hearing, and tingling sensations. This document refers to monitoring a patient to determine when the patient may be at risk of syncope induced by posture changes, which is also intended to include, unless otherwise noted, when the patient is at risk of pre-syncope symptoms that may or may not ultimately cause the patient to lose consciousness. If neural stimulation is being delivered to reduce sympathetic tone/ increase parasympathetic tone, the activation of this neural stimulation at the time of posture-induced BP/HR reduction may override this normal reflex to normalize BP/HR, and may place the patient at risk of a prolonged, potentially serious reduction in BP/HR, which may result in syncope.

FIG. 1 illustrates a transition between posture states indicative of a risk of syncope, and the therapy override to ameliorate the risk of syncope according to an example of the present subject matter. In the example provided the illustrated embodiment, the present subject matter detects a posture transition 100 between a first posture state 101 and a second posture state 102. As further discussed below, this posture transition may be considered to increase the patient's risk of syncope. The present subject matter may control neural stimulation (e.g. override a normally-delivered neural stimulation therapy) during the posture transition to reduce this risk. Often, posture syncope may occur as the patient assumes an upright position. However, the present subject matter is not necessarily limited to posture changes to the upright position. Changes in posture may include, by way of example and not limitation, a change from a more upright posture to a more recumbent posture, a change from a more recumbent posture to a more upright posture, and a change within a recumbent posture (e.g. change from supine to a right or left lateral decubitus). By way of example and not limitation, some neural stimulation therapies may be a parasympathetic therapy that increases parasympathetic tone and decreases sympathetic tone in the patient. An example of such a system is a barostimulation system. For systems that deliver such parasympathetic therapy, some embodiments may reduce or stop the parasympathetic therapy when the patient is at risk of syncope to allow the patient's natural baroreflex response to normalize BP/HR levels. Thus, for example, the present subject matter may be configured to detect when a patient transitions between posture states in a manner that can induce BP/HR reduction, such as from a reclined position to an upright position, and may be configured to control delivery of such neural stimulation to avoid the neural stimulation from coinciding with a BP/HR reduction induced by the posture change or to reduce the therapy during and/or after this change. Some neural stimulation may be a sympathetic therapy that increases sympathetic tone and decreases parasympathetic tone. For systems that deliver such sympathetic therapy, some embodiments may deliver or increase the sympathetic therapy when the patient is at risk of syncope to quickly increase sympathetic tone, which quickly increase blood pressure. The present subject matter may be implemented with external neural stimulation systems, and may be implemented with implantable neural stimulation systems.

Types of neural stimulation therapies that may quickly affect blood pressure include peripheral nerve stimulation such as stimulation of the vagus nerve, carotid sinus nerve or glossopharyngeal nerve. Vagal nerve stimulation has been proposed to treat many conditions, such as cardiac conditions such as heart failure and arrhythmias, hypertension, pain, epilepsy, eating disorders, depression. Neural stimulation therapies to treat hypertension may target the baroreflex response, such as by stimulating the vagus nerve, the carotid sinus nerve, the glossopharyngeal nerve, baroreceptor regions and/or chemoreceptor regions. Baroreceptor regions include the carotid sinus baroreceptors and pulmonary artery baroreceptors. Other neural stimulation therapies that can quickly affect blood pressure include spinal cord stimulation (SCS) and deep brain stimulation. SCS has been shown to have a sympatholytic effect. These effects are mediated either directly through modulation of sympathoefferent spinal circuits or indirectly by peripheral vasodilation via spinal-mediated nerve traffic, similar to dorsal root reflexes. Dermatomes for intercostal nerves (the ventral or anterior divisions of the thoracic spinal nerve) may be stimulated. Peripheral nerve field stimulation (PNFS) also may be used to modulate the autonomic balance. For example, an area of skin innervated by a peripheral nerve may be used to modulate the autonomic balance.

Figure 2:
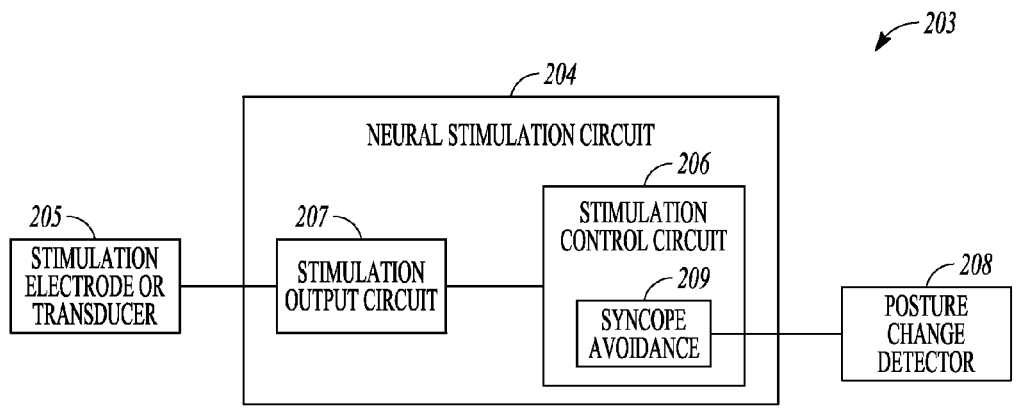
FIG. 2 illustrates, by way of example and not limitation, and embodiment of a neural stimulation system with a syncope avoidance routine to reduce a risk of postural syncope.

FIG. 2 illustrates, by way of example and not limitation, and embodiment of a neural stimulation system with a syncope avoidance routine to reduce a risk of postural syncope. The illustrated system 203 includes a neural stimulation circuit 204 and a stimulation electrode or transducer 205 configured for use to stimulate a neural target of a patient. The illustrated neural stimulation circuit 204 includes a stimulation control circuit 206 and a stimulation output circuit 207. The control circuit 206 controls the neural stimulation output circuit 207 to deliver the desired stimulation through the stimulation electrode or transducer 205. By way of example and not limitation, the prescribed neural stimulation delivered to the patient may be programmed into the device to deliver a desired dose of neural stimulation according to a programmed schedule. Some embodiments do not include a physiological sensor connected to the control circuit to automatically titrate the dose of the neural stimulation to achieve a desired physiological parameter (e.g. heart rate or blood pressure) for the stimulation. Thus, it is considered an open-loop control system. Other embodiments, such as the example illustrated in FIG. 14, may include a physiological sensor connected to the control circuit to provide stimulation feedback of a physiological parameter for use to automatically titrate the dose of the neural stimulation to achieve a desired value for the physiological parameter (e.g. heart rate or blood pressure). Such systems are referred to as close-loop control systems. The syncope avoidance routine of the present subject matter may be implemented with either open loop or closed loop control systems.

The illustrated system 203 includes a posture change detector 208 configured to detect a change in posture that is considered significant for increasing the risk of syncope, allowing the stimulation control circuit 206 to implement a syncope avoidance routine 209 to reduce the risk of syncope attributable to the posture routine. To clarify, the posture change detector does not provide stimulation feedback to automatically titrate the dose of the neural stimulation. Rather, the posture change detector detects a change in posture indicating an increased risk of syncope, allowing the neural stimulation to be controlled to counter this increased risk attributable to the posture change.

Figure 3:
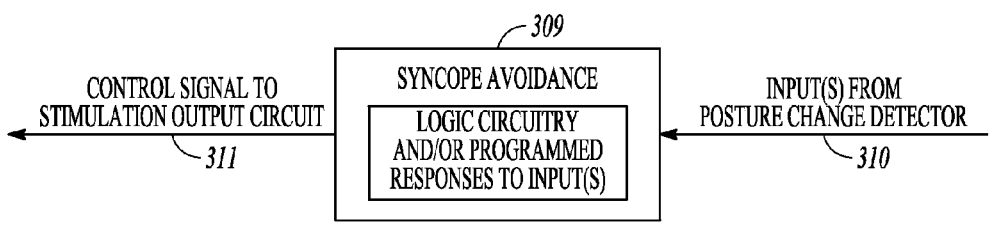
FIG. 3 illustrates, by way of example and not limitation, an embodiment of a syncope avoidance module that may be integrated with or part of the stimulation control circuit.

FIG. 3 illustrates, by way of example and not limitation, an embodiment of a syncope avoidance module that may be integrated with or part of the stimulation control circuit. The illustrated syncope avoidance module 309 receives one or more inputs 310 from the posture change detector. In some embodiments, the posture change detector is configured to only send a signal when the posture change is significant enough to warrant the syncope avoidance. In some embodiments, the posture change detector is configured to send signals, operable on by the syncope avoidance module, to determine when the patient is at an increased risk of syncope that is substantial enough to warrant syncope avoidance. The syncope avoidance module may be implemented using hardware, software, firmware, or various combinations thereof. For example, the syncope avoidance module may be implemented used logic circuitry and/or programmed responses to input(s) from the posture change detector. If syncope avoidance is warranted, the syncope avoidance module 309 sends a signal 311 to appropriately control the stimulation output circuit, thus overriding a normally-delivered neural stimulation therapy. For example, parasympathetic stimulation may be temporarily reduced or disabled for a period of time, or sympathetic stimulation may be temporarily increased or enabled for a period of time to allow the blood pressure to quickly raise, thus reducing the risk of posture-induced syncope.

Figure 4:
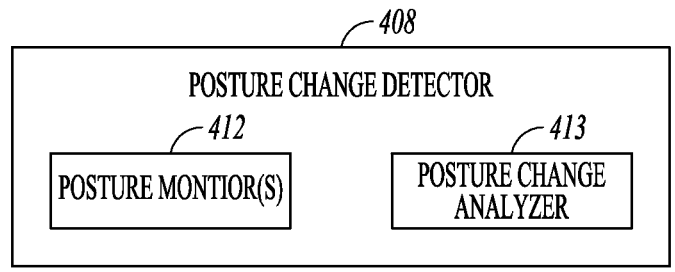
FIG. 4 illustrates, by way of example and not limitation, an embodiment of a posture change detector.

FIG. 4 illustrates, by way of example and not limitation, an embodiment of a posture change detector. For example, the posture change detector 408 may include one or more posture monitors 412 which include one or more sensors that provide a signal indicative of the orientation of the sensor(s), which may be used to determine a posture state. The posture monitor may also include signal processing to convert a sensor signal into digital data that may be processed. For a tilt switch, the conversion may be simply recognizing the switch as open or closed, where one state indicates a recumbent patient and the other state indicates a non-recumbent patient. For an accelerometer, the processing circuitry may amplify and/or filter the accelerometer signal prior to conversion to digital data to maintain a sufficient granularity for more precisely determining the degree of reclination of the body. The processing circuitry may provide reclination data where the degree of reclination of the body can be factored into controlling neural stimulation to avoid syncope. The posture change detector 408 may further include a posture change analyzer 413 configured to analyze posture changes to identify posture changes that are significant enough to be considered to increase the risk of postural syncope, and thus warrant controlling the neural stimulation to counter this increased risk of syncope. Thus, by way of example, if the neural stimulation therapy normally reduces blood pressure, the therapy may be temporarily reduced or the therapy may be temporarily stopped to allow the baroreflex to raise blood pressure.

Figure 5:
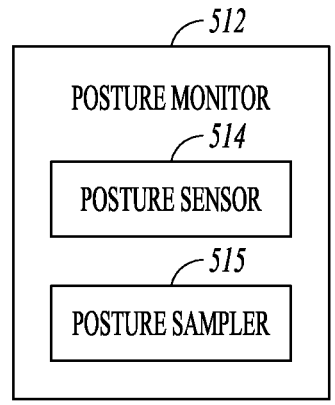
FIG. 5 illustrates, by way of example and not limitation, an embodiment of a posture monitor.

FIG. 5 illustrates, by way of example and not limitation, an embodiment of a posture monitor. The illustrated posture monitor 512 includes a posture sensor 514 and a posture sampler 515. The posture sensor 514 may be used to determine the orientation of the sensor (and thus a posture state of the patient) at a given time. The posture sampler 515 controls when the posture sensor determines the posture state of the patient, enabling the posture monitor 512 to monitor for posture changes that may increase the risk of postural syncope. The sampling of posture, rather than continuously sensing posture, reduces power requirements. Implantable medical devices are operated using batteries, and significant design considerations for these devices include power requirements, as it is desirable to extend battery life and avoid procedures for replacing or recharging batteries.

Figure 6:
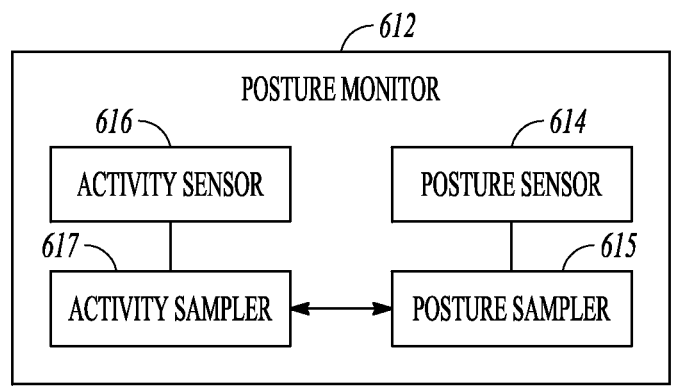
FIG. 6 illustrates, by way of example and not limitation, an embodiment of a posture monitor that uses activity to control the sampling of the patient's posture.

Currently, posture sensor technology requires significant power, such that continuous "sampling" of posture at a rate sufficient to detect posture transitions may consume an undesirable amount of power. Some embodiments use lower-power activity sensors to sample the patient's activity, and trigger posture sampling by the posture detector when the patient's activity indicates that the patient may be transitioning between posture states. FIG. 6 illustrates, by way of example and not limitation, an embodiment of a posture monitor that uses activity to control the sampling of the patient's posture. The illustrated posture monitor 612 includes one or more posture sensors 614 and one or more activity sensors 616. The illustrated posture monitor 612 further an activity sampler 617 used to control the sensing of activity by the activity sensor 616, and a posture sampler 615 used to enable the sensing of posture by the posture sensor 614. The activity sampler 617 may be configured to enable the posture sampler 615 when the patient's activity indicates that the patient may be changing the posture. Thus, activity sensor(s), with lower power requirements, may be used to determine when the patient's posture should be sampled. Additionally, in some embodiments, for example, the activity data may be used with the posture data to provide blended data that further refine posture changes/activity levels that are considered to increase the risk of syncope. For example, a high activity level may indicate that the patient autonomic tone has already increased to meet a higher metabolic demand for the patient. A posture change at a time when the patient already is at a high activity level may not be considered to be a syncope risk, whereas a posture change with a low activity level may be considered to be a syncope risk since the patient's naturally occurring baroreflex would not have an opportunity to raise the sympathetic tone to increase blood pressure.

Some embodiments may use one or more posture sensors, such as a 3-axis DC-sensitive accelerometer, to detect posture shifts that may place the patient at risk of syncope. Posture sensors may include one or more tilt switches, one or more single axis accelerometers such as a DC-sensitive accelerometer, and/or one or more multi-axis accelerometers. The posture sensor(s) may include internal posture sensor(s) and/or external posture sensor(s). By way of example and not limitation, a posture sensor may be implanted with the neural stimulator in the torso of the patient. The posture sensor may be configured to detect the posture state of the patient (e.g. lying, reclining, upright) and/or may be configured to detect a degree of reclination. A posture sensor may be designed with three accelerometers, each operative in a separate axis, used to detect tilt in any direction. Additionally, multiple posture sensors may be used and coordinated to detect not only the torso orientation, but also the orientation of the patient's legs (e.g. thigh) or head. Such additional posture sensors can be used to provide more complete information about the patient's posture (e.g. standing upright or sitting upright). The communication between or among posture sensors may be implemented using wired or wireless technologies. Examples of wireless communication technologies include, but are not limited to, radio frequency, inductive, and ultrasound communications. The posture sensor may detect reclination, producing an electrical signal that is representative of the orientation of the sensor relative to gravity. In either case, a signal is produced by the sensor in response to the sensor having a particular orientation relative to gravity. Therefore, the sensor is coupled to the body, either externally or internally, with a known orientation so that the reclination sensor produces a detectable signal in response to the body having an orientation with respect to gravity. By way of example, and not limitation, the signal may indicate whether the patient is in a recumbent or non-recumbent state. The sensor may be multi-axis responsive so that regardless of the orientation of the body while in a recumbent position (i.e., lying on back versus lying on side), a detectable signal is produced. A 3-axis posture detector may be associated with device coordinate axes U, V, and W. The posture detector may comprise one or more uniaxial orientation sensors, for example, three uniaxial DC accelerometers. Each device coordinate axis, U, V, or W, corresponds to a sensitive axis of one uniaxial accelerometer of the posture detector, which are typically arranged in a mutually orthogonal orientation. The sensitive axes of the uniaxial accelerometers U, V, and W may not be aligned perfectly with respect to the gravitational acceleration vector G acting on the patient's body. In a typical implant implementation, the device axes are tilted slightly or significantly with respect to the vector G. Further, the device axes U, V, and W are not necessarily aligned with body coordinates X, Y, and Z. The three uniaxial accelerometers may be formed as an integrated device such as a surface micro-machined semiconductor device. In one implementation, each uniaxial accelerometer comprises an inertial mass suspended by compliant springs which are acted on by gravity. The magnitude of the inertial mass deflection is converted to an electrical signal by the surrounding electronics and appears as the sensor output of the uniaxial accelerometer. The output of an accelerometer acted on by the earth's gravitational force provides a characteristic DC output voltage, e.g., maximum output, if the sensitive axis of the accelerometer is aligned with the earth's gravitational field while the accelerometer is at rest. As the patient's body moves, the angle at which the sensitive axis of the accelerometer is tilted with respect to the earth's gravitation force changes and the output of the accelerometer is related to the angle of tilt.

Figure 7:
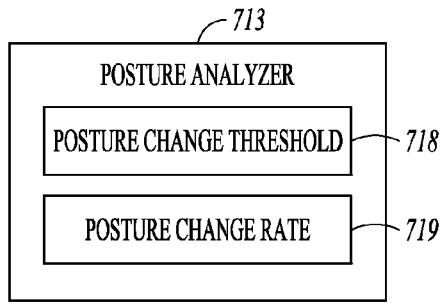
FIG. 7 illustrates an example of a posture analyzer 713 that considers both a threshold posture 718 and a rate of posture change 719.
Figure 8:
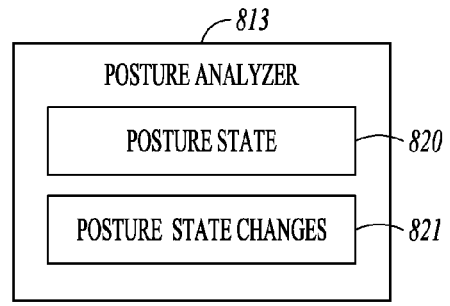
FIG. 8 illustrates an example of a posture analyzer 843 that considers a posture state 820, and changes 821 between posture states.
Figure 9:
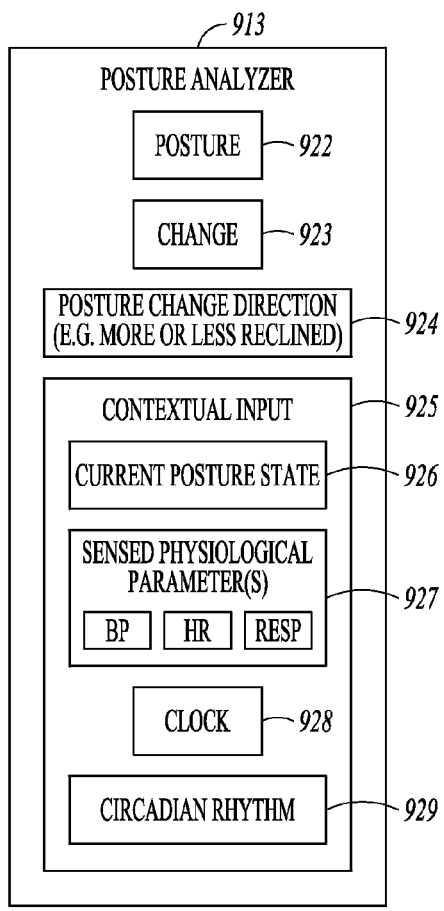
FIG. 9 illustrates an example of a posture analyzer 913 that monitors posture 922, a posture change 923 and a direction 924 of a posture change.
Figure 10:
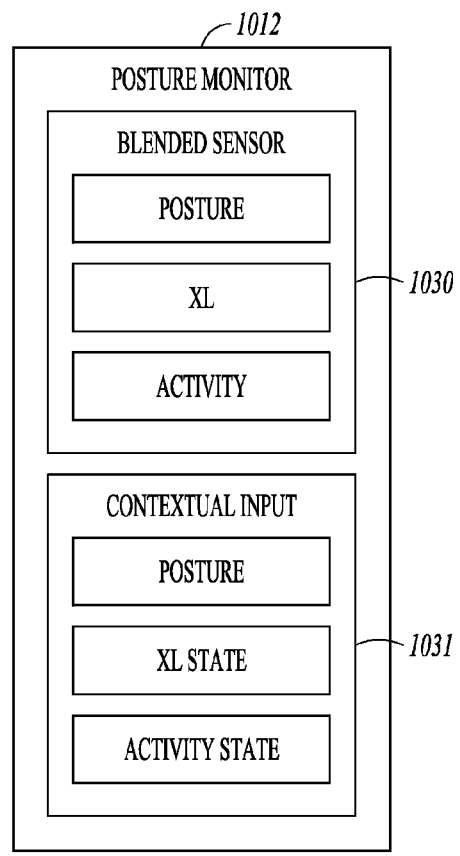
FIG. 10 illustrates an example of a posture monitor 1014 that uses blended sensor 1030 to determine a posture state 1031 and posture changes between states.

FIGS. 7-10 illustrate, by way of example and not limitation, various embodiments that may be implemented to determine when the posture change significantly increases a risk of syncope. FIG. 7 illustrates an example of a posture analyzer 713 that considers both a threshold posture 718 and a rate of posture change 719. For example, if the inclination angle changes by a certain magnitude ("threshold") over a period of less than a certain amount of time ("rate"), then the analyzer may determine that the patient is at an increased risk of syncope because the posture is changing substantially and quickly. FIG. 8 illustrates an example of a posture analyzer 843 that considers a posture state 820, and changes 821 between posture states. For example, the analyzer may determine that the risk syncope increases for a patient who changes from posture state 1 to posture state 2 (e.g. lying down to standing up). FIG. 9 illustrates an example of a posture analyzer 913 that monitors posture 922, a posture change 923 and a direction 924 of a posture change. Thus, for example, the analyzer may determine that the risk of syncope increases only if the patient is moving toward a more upright position from a particular posture state. By way of example, the system may control neural stimulation to avoid syncope if the patient is lying down, and the posture changes toward a more inclined position from this position. Further, the analyzer 913 may include contextual inputs 925. For example, the analyzer may be configured to provide specific responses to changes between specific past and specific current posture states 926. A change from a lying down position to a reclined position may produce a first analysis result, whereas a change from a lying down position to an upright position may be produce a second analysis result and a change from a reclined position to an upright position may produce a third analysis result. One or more sensed physiological parameters 927 may be used to provide context. For example, blood pressure, heart rate, and/or respiration may be used to determine a current physiological state of the patient, which may also be used to determine the likelihood that a posture change may result in a posture-induced syncope. Another example of contextual inputs that may be used alone or in combination with other contextual inputs includes a clock 928. The clock may be used to estimate times of higher and lower activity. Another example of a contextual input that may be used with or without a monitored physiological parameter is a circadian rhythm template for the patient 929. For example, the template may represent the normal fluctuations that occur for a monitored physiological parameter over the course of a day. The analyzer may be used to determine that syncope is more likely to occur at certain times of day and/or at certain activity levels. FIG. 10 illustrates an example of a posture monitor 1014 that uses blended sensor 1030 to determine a posture state 1031 and posture changes between states. For example, a posture sensor, and accelerometer, and/or an activity sensor may be used to determine a patient state (e.g. a posture state, an accelerometer state, and/or an activity state). Such a blended sensor may be used to provide a more nuanced detection of a patient attempting to change posture. For example, an activity sensor in combination with a posture sensor may be used to detect the patient's efforts to change posture, which also indicates increased metabolic demand. Such a blended combination may be useful to quickly detect a posture transition that is considered to provide an increased risk of syncope.

In an example a posture sensor may operate at a low sample rate on the order of one sample per minute, by way of example and not limitation, to conserve battery energy in the implanted device, whereas a more energy-efficient activity sensor can continuously operate at a higher sample rate. In this example, when the continuously operating activity sensor detects a certain level of activity, it may trigger the posture sensor to temporarily sample more rapidly to make a quick assessment of possible posture change associated with the activity. If the posture change is determined sufficiently quickly, therapy can be provided to prevent a syncopal event, perhaps by pacing the heart at an increased rate.

Figure 11:
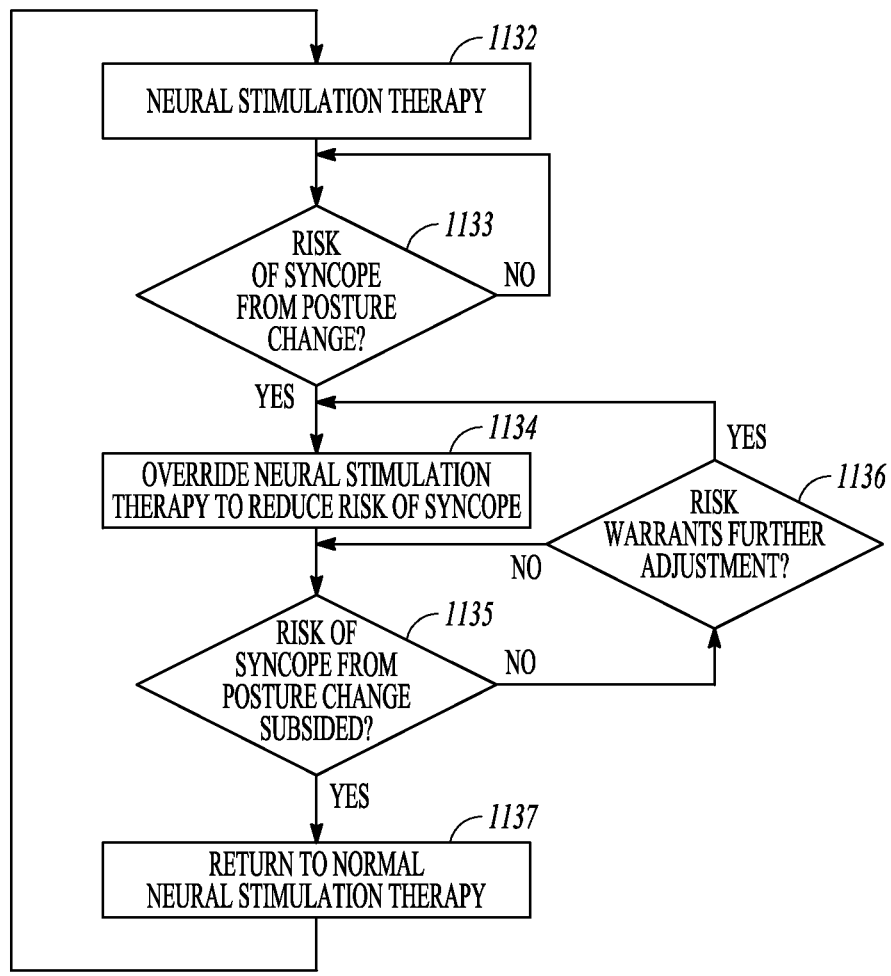
FIG. 11 illustrates, by way of example and not limitation, an embodiment for controlling neural stimulation to reduce a risk of postural syncope.

FIG. 11 illustrates, by way of example and not limitation, an embodiment for controlling neural stimulation to reduce a risk of postural syncope. A neural stimulation therapy is applied at 1132. The stimulation therapy may be delivered as a train of neural stimulation pulses. Further, the stimulation therapy may be intermittent, in which a train of stimulation pulses are delivered during a stimulation ON period, no stimulation pulses are delivered during a subsequent stimulation OFF period, and another train of stimulation pulses are delivered during a stimulation ON period after the stimulation OFF period. The train of pulses may be also referred to as a stimulation burst of pulses. Intermittent neural stimulation therapies may be delivered according to a programmed schedule, such as may be used to chronic therapies to treat hypertension or heart failure, for example. Neural stimulation may also be initiated and/or stopped in response to triggering events. For example, a blood pressure sensor may be used to sense a high blood pressure threshold and a low blood pressure threshold. A neural stimulation therapy that targets the baroreflex to increase parasympathetic activity/reduce sympathetic activity may be triggered on when the high blood pressure threshold is sensed, and may be triggered off when the low blood pressure threshold is sensed. The neural stimulation therapy illustrated at 1132 is intended to include a normal neural stimulation therapy for treating a condition which may include constant stimulation (e.g. a continual train of stimulation pulses) or intermittent stimulation (e.g. either programmed schedule of stimulation ON and stimulation OFF periods, or triggered stimulation ON and stimulation OFF periods). The present subject may be considered to override the normal neural stimulation therapy when there is a risk of syncope from a posture change, allowing the system to take appropriate action to allow the patient's baroreflex response to ameliorate the risk of syncope induced by a posture change.

At 1133, the illustrated process determines if there is a risk of syncope from a posture change. This may be detecting a change from a first posture state (e.g. reclined) to a second posture state (upright). Some embodiments allow the system to be programmed with patient-specific information. For example, a patient may be aware that posture-induced syncope tends to occur during certain posture changes. The patient may be asked to mimic those positions and the posture change between those positions, and the appropriate values from the posture sensors may be recorded and used to detect a risk of syncope in an ambulatory patient.

At 1134, if the system determines that there is a risk of postural syncope, the illustrated process takes appropriate action to ameliorate the risk of syncope from the posture change. For example, if the system is delivering neural stimulation that elicits a parasympathetic response (e.g. baroreflex stimulation), then the neural stimulation be reduced or stopped during the posture transition, thus allowing the blood pressure to rise during the posture change to ameliorate the risk of posture-induced syncope. If the neural stimulation is an intermittent neural stimulation, some embodiments may prevent neural stimulation during the posture transition or for a period of time after the posture transition. Furthermore, some embodiments may allow the neural stimulation that began before the posture transition to continue; but if intermittent neural stimulation is in a stimulation OFF period when the posture change occurs, some embodiments will override the normal therapy by preventing the neural stimulation ON period until a period of time after the posture transition. It is currently believed that the patient may experience greater blood pressure reduction at the beginning of a train of stimulation pulses, and thus may be more susceptible to syncope during a posture transition at the beginning of a stimulation burst. If the system is capable of delivering neural stimulation that elicits a sympathetic response, such as may occur by stimulating neural activity in a sympathetic nerve or inhibiting neural activity in a parasympathetic nerve, then the neural stimulation therapy may be initiated or adjusted to increase sympathetic tone, thus raising blood pressure during the posture change to ameliorate the risk of posture-induced syncope.

At 1135, the illustrated process may determine if the risk of syncope from the posture change has subsided. If the risk remains, and if the risk warrants further adjustment as illustrated at 1136, then the neural stimulation therapy may be further adjusted as part of the override of the normal therapy caused by the posture change. If the risk subsided, then the process proceeds to 1137 to return to the normal neural stimulation therapy.

Figure 12:
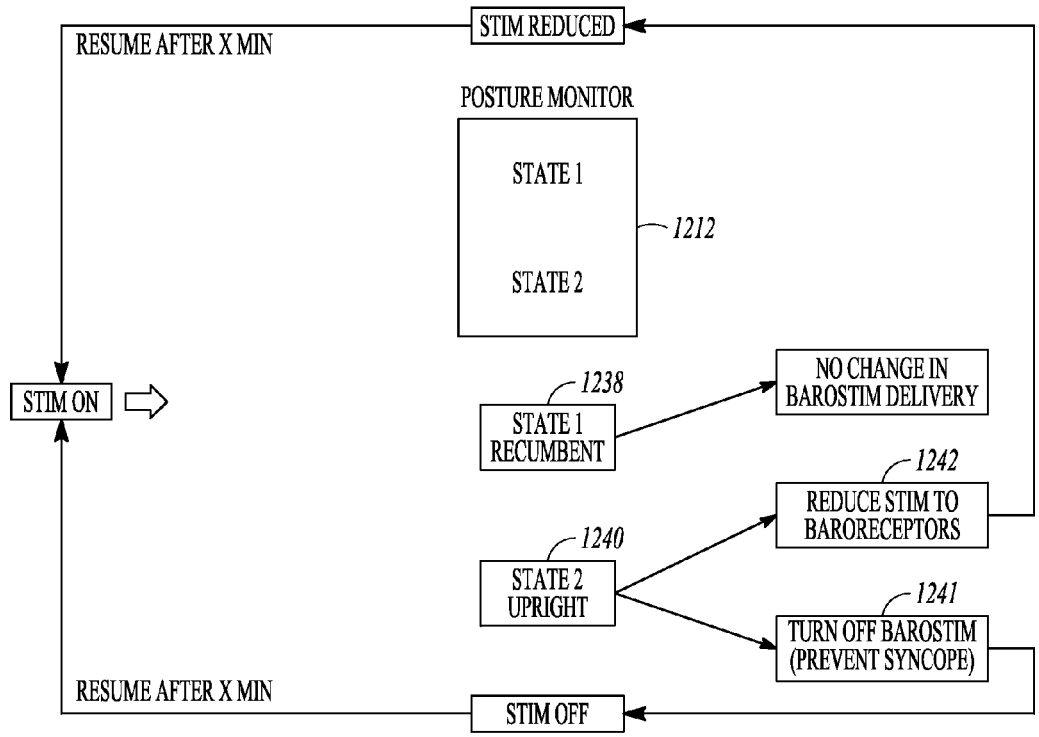
FIG. 12 illustrates an example of a process that may be performed by an embodiment of a barostimulation system.

FIG. 12 illustrates an example of a process that may be performed by an embodiment of a barostimulation system. For example, a baroreflex response may be caused by stimulation a vagus nerve, a carotid sinus nerve, a glossopharyngeal nerve, baroreceptor regions such as baroreceptor regions in the carotid sinus or in the pulmonary artery, chemoreceptor regions, and cardiac fat pads. The illustrated system refers to, by way of example and not limitation, barostimulation delivered to baroreceptor sites. A normally-delivered barostimulation therapy may be delivered to treat a variety of conditions, such as the chronic conditions of hypertension or heart failure. A posture monitor 1212 may detect two states: Recumbent (State 1) and Upright (State 2). If the patient is in the recumbent state 1238, then there is no change in the normally delivered barostimulation therapy 1239. If the patient moves to the upright state 1240, then the normal barostimulation therapy is overridden for a temporary period of time (e.g. X minutes) to ameliorate the risk of posture-induced syncope. In the illustrated embodiment, the barostimulation may be temporarily turned off 1241, or the barostimulation may be temporarily reduced 1242. Furthermore, some embodiments may implement a tiered approach to the override. By way of example, during the temporary period of time in which the normal barostimulation is overridden, some embodiments may turn of the barostimulation for a first portion of the period, and then turn on the stimulation at a reduced intensity for a second portion. In embodiments that reduce intensity of the barostimulation, some embodiments may ramp up the barostimulation intensity over time using one or more intermediate intensity levels to return to the normal barostimulation therapy. Such a ramp-up stimulation protocol after the posture transition may further reduce the risk of syncope.

Figure 13:
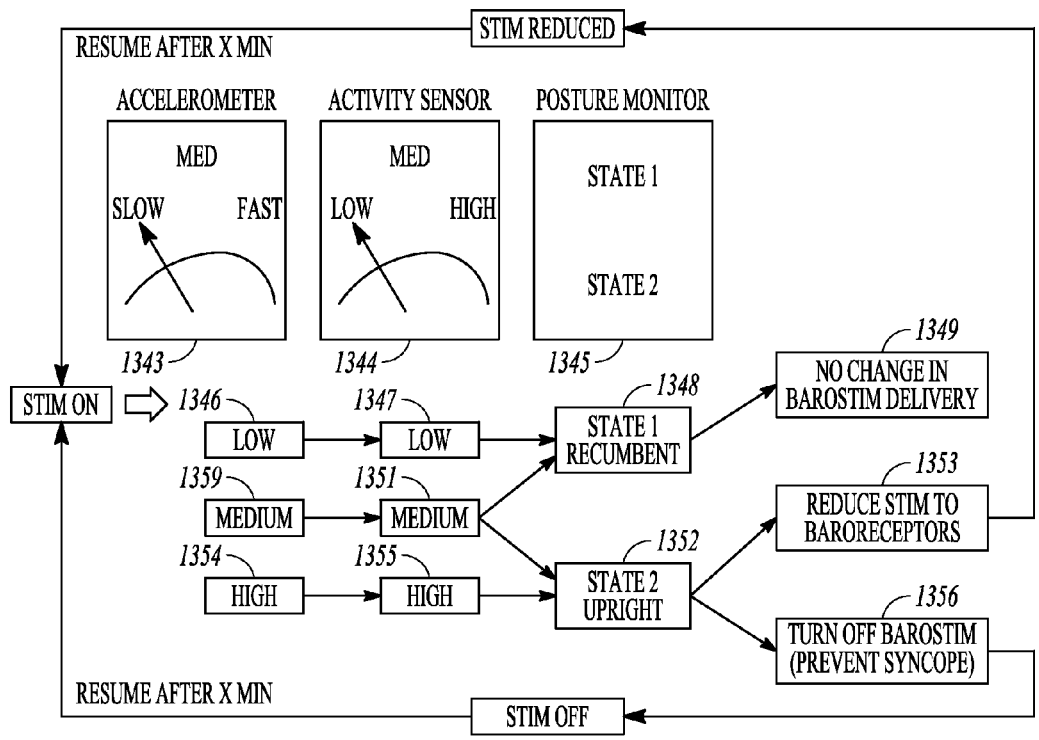
FIG. 13 illustrates an example of a process that may be performed by an embodiment of a barostimulation system that includes blended sensor information.

FIG. 13 illustrates an example of a process that may be performed by an embodiment of a barostimulation system that includes blended sensor information. The illustrated embodiments may include an accelerometer 1343, an activity sensor 1344, and a posture monitor 1345. The posture monitor may be configured to detect two states: Recumbent (State 1) and Upright (State 2). The accelerometer may be configured to distinguish between a low, medium and high state, and the activity sensor may also be configured to distinguish between a low, medium and high state. In the illustrated embodiment, if the accelerometer is low 1346, the activity sensor is low 1347, and the posture is recumbent 1348, then the system may determine that there should be no change in the normally-delivered barostimulation therapy 1349. If the accelerometer is medium 1350, the activity sensor is medium 1351, and the posture is recumbent 1348, then the system may determine that there should be not change in the normally-delivered barostimulation therapy 1349. If the accelerometer is medium 1350, the activity sensor is medium 1351, and the posture is upright 1352, then the system may determine that the barostimulation therapy should be temporarily reduced for a period to time (e.g. x minutes) 1353. If the accelerometer is high 1354, the activity sensor is high 1355, and the posture is upright 1352, then the system may determine that the barostimulation therapy should be temporarily turned off for a period to time (e.g. x minutes) 1356. These specific combinations are provided as examples, and are not intended to be limiting and are not intended to be an exhaustive list. There are other potential combinations of these sensors (e.g. low accelerometer, medium activity and upright position), and the system may be configured to provide a specific response to these potential combinations. Also, the example is not intended to indicate the only possible response to accelerometer, activity and posture inputs.

Figure 14:
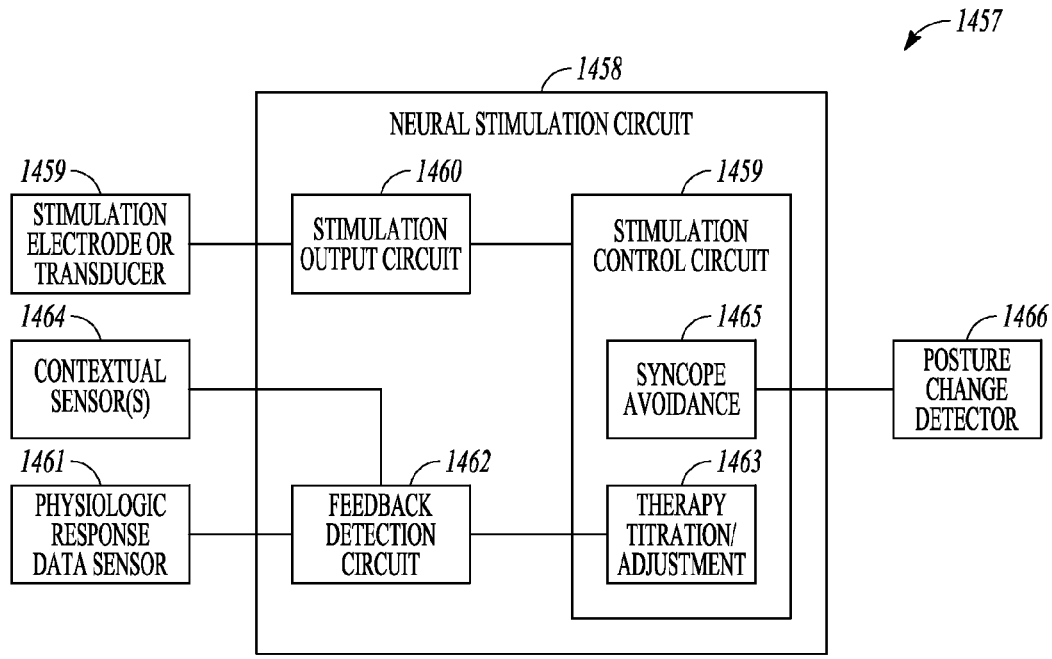
FIG. 14 illustrates, by way of example and not limitation, an embodiment of a neural stimulation circuit with a syncope avoidance routine to reduce a risk of posture-induced syncope.

FIG. 14 illustrates, by way of example and not limitation, an embodiment of a neural stimulation circuit with a syncope avoidance routine to reduce a risk of posture-induced syncope. The circuit has some similarities to the circuit of FIG. 2. However, whereas the neural stimulation in FIG. 2 has an open loop control system, the neural stimulation in FIG. 14 receives feedback for a closed-loop control system. The illustrated system 1457 includes a neural stimulation circuit 1458 and a stimulation electrode or transducer configured for use to stimulate a neural target of a patient. The illustrated neural stimulation circuit 1458 includes a stimulation control circuit 1459 and a stimulation output circuit 1460. The control circuit 1457 controls the neural stimulation output circuit 1460 to deliver the desired stimulation through the stimulation electrode or transducer. The illustrated system includes a physiological response sensor 1461 and feedback detection circuit 1462 connected to the control circuit 1459 to provide stimulation feedback of a physiological parameter for use to automatically titrate the dose of the neural stimulation, via the therapy titration/adjustment module 1463 in the stimulation control circuit 1459, to achieve a desired value for the physiological parameter (e.g. heart rate or blood pressure). Such systems are referred to as closed loop control systems. This close-loop control of the neural stimulation may be considered to be the normal neural stimulation therapy. The normal stimulation may also use contextual sensor(s) 1464 to interpret the sensed physiological response. Thus, for example, the feedback detection circuit 1462 may receive patient activity information along with the sensed physiological response (e.g. blood pressure, heart rate, respiration), and determine that the increased in blood pressure is warranted to accommodate the increased metabolic demand to support the higher activity. Examples of contextual sensor(s) or input(s) include but are not limited to activity, time, and environment such as temperature, humidity, altitude. The syncope avoidance routine 1465 may be implemented to override the normal neural stimulation therapy. The illustrated system includes a posture change detector 1466 configured to detect a change in posture that is considered significant for increasing the risk of syncope, allowing the stimulation control circuit to implement a syncope avoidance routine to reduce the risk of syncope attributable to the posture routine. The posture change detector detects a change in posture indicating an increased risk of syncope, allowing the neural stimulation to be controlled to counter this increased risk attributable to the posture change.

Figure 15:
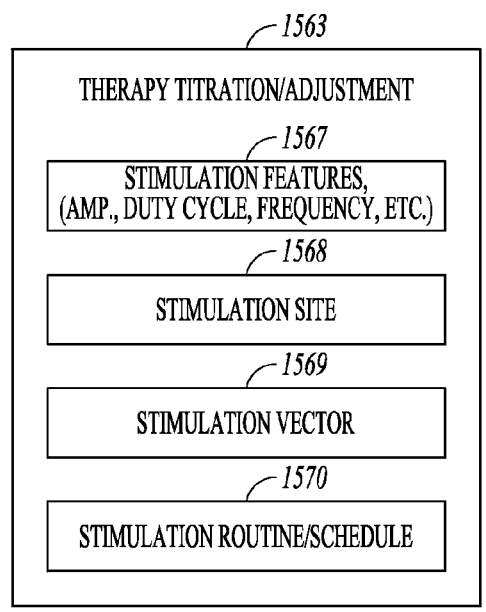
FIG. 15 illustrates, by way of example, an embodiment of a therapy titration module 1563 such as is illustrated at 1463 in FIG. 14.

FIG. 15 illustrates, by way of example, an embodiment of a therapy titration module 1563 such as is illustrated at 1463 in FIG. 14. According to various embodiments, the stimulation control circuit is adapted to set or adjust any one or any combination of stimulation features 1567. Examples of stimulation features include the amplitude, frequency, polarity and wave morphology of the stimulation signal. Examples of wave morphology include a square wave, triangle wave, sinusoidal wave, and waves with desired harmonic components to mimic naturally-occurring baroreflex stimulation. Some embodiments of the stimulation output circuit are adapted to generate a stimulation signal with a predetermined amplitude, morphology, pulse width and polarity, and are further adapted to respond to a control signal from the controller to modify at least one of the amplitude, wave morphology, pulse width and polarity. Some embodiments of the neural stimulation circuitry are adapted to generate a stimulation signal with a predetermined frequency, and are further adapted to respond to a control signal from the controller to modify the frequency of the stimulation signal.

The therapy titration module 1563 can be programmed to change stimulation sites 1568, such as changing the stimulation electrodes used for a neural target or changing the neural targets for the neural stimulation. For example, different electrodes of a multi-electrode cuff can be used to stimulate a neural target. Examples of neural targets include the right and left vagus nerves, cardiac branches of the vagus nerve, cardiac fats pads, baroreceptors, the carotid sinus, the carotid sinus nerve, and the aortic nerve. Autonomic neural targets can include afferent pathways and efferent pathways and can include sympathetic and parasympathetic nerves. The stimulation can include stimulation to stimulate neural traffic or stimulation to inhibit neural traffic. Thus, stimulation to evoke a sympathetic response can involve sympathetic stimulation and/or parasympathetic inhibition; and stimulation to evoke a parasympathetic response can involve parasympathetic stimulation and/or sympathetic inhibition.

The therapy titration module 1563 can be programmed to change stimulation vectors 1569. Vectors can include stimulation vectors between electrodes, or stimulation vectors for transducers. For example, the stimulation vector between two electrodes can be reversed. One potential application for reversing stimulation vectors includes changing from stimulating neural activity at the neural target to inhibiting neural activity at the neural target. More complicated combinations of electrodes can be used to provide more potential stimulation vectors between or among electrodes. One potential stimulation vector application involves selective neural stimulation (e.g. selective stimulation of the vagus nerve) or changing between a selective stimulation and a more general stimulation of a nerve trunk.

The therapy titration module 1563 can be programmed to control the neural stimulation according to stimulation instructions, such as a stimulation routine or schedule 1570, stored in memory. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time. Duty cycle is specified by the ON time and the cycle time, and thus can have units of ON time/cycle time. According to some embodiments, the control circuit controls the neural stimulation generated by the stimulation circuitry by initiating each pulse of the stimulation signal. In some embodiments, the stimulation control circuit initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the stimulation control circuit controls the stimulation output circuit to initiate a neural stimulation session and to terminate the neural stimulation session. The burst duration of the neural stimulation session under the control of the control circuit can be programmable. The controller may also terminate a neural stimulation session in response to an interrupt signal, such as may be generated by one or more sensed parameters or any other condition where it is determined to be desirable to stop neural stimulation. A neural stimulation embodiment may include a programmed therapy schedule or routine stored in memory and further includes a clock or timer which can be used to execute the programmable stimulation schedule. For example, a physician can program a daily/weekly schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session. According to various embodiments, the stimulation schedule refers to the time intervals or period when the neural stimulation therapy is delivered. A schedule can be defined by a start time and an end time, or a start time and a duration. Various schedules deliver therapy periodically. By way of example and not limitation, a device can be programmed with a therapy schedule to deliver therapy from midnight to 2 AM every day, or to deliver therapy for one hour every six hours, or to deliver therapy for two hours per day, or according to a more complicated timetable. Various device embodiments apply the therapy according to the programmed schedule contingent on enabling conditions, such as sensed exercise periods, patient rest or sleep, low heart rate levels, and the like. For example, the stimulation can be synchronized to the cardiac cycle based on detected events that enable the stimulation. The therapy schedule can also specify how the stimulation is delivered.

Figure 16:
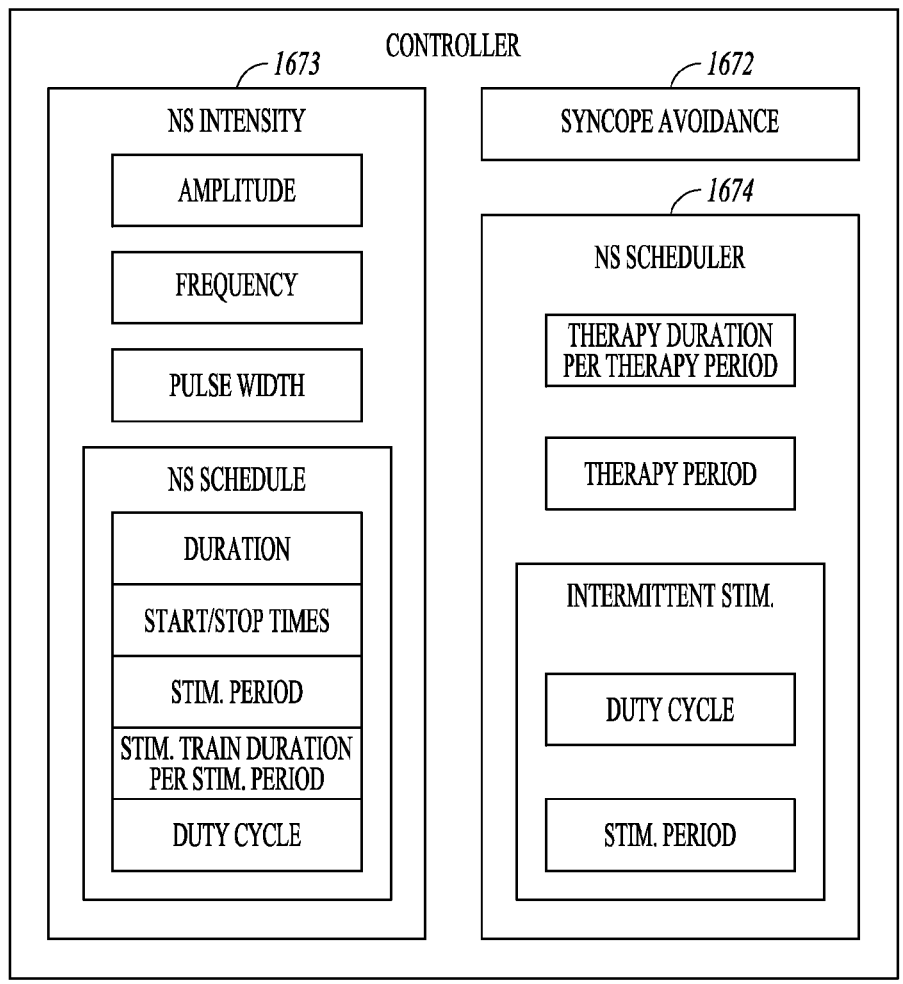
FIG. 16 illustrates, by way of example not limitation, an embodiment of a controller for a neural stimulation device.

FIG. 16 illustrates, by way of example not limitation, an embodiment of a controller for a neural stimulation device. The controller 1671 appropriately controls the neural stimulation therapy delivery system to provide the appropriate neural stimulation signal to the electrode(s) for a desired neural stimulation therapy, and further includes a syncope avoidance module 1672 to override this therapy. The controller implements the neural stimulation therapy using the programmable parameters. Examples of programmable parameters, any one or more of which can be stored in a memory, include a therapy duration parameter, a therapy period, as well as a duty cycle, and a stimulation therapy for intermittent stimulation. The programmable parameters can also include parameters used to adjust the intensity of the neural stimulation therapy 1673, such as amplitude, frequency, pulse width, and stimulation schedule parameters.

The illustrated device includes a neural stimulation scheduler 1674, which may use a clock/timer along with schedule parameter(s) to control the stimulation delivered by the delivery system. In some embodiments, the neural stimulation controller controls the neural stimulation to provide a chronic therapy for a chronic condition, such as hypertension or heart failure. The scheduler uses at least one schedule parameter. Some scheduler embodiments use a duration parameter(s) to control the therapy duration per therapy period, and some scheduler embodiments use a therapy period parameter to control a duration of time before a subsequent therapy is applied. For example, some embodiments use a therapy period of approximately one day, and use a therapy duration of approximately 8 hours each day. These parameter(s) can represent limits (e.g. maximum, minimum, range) for the parameter values. Some embodiments, for example, use the therapy duration parameter as a minimum value, such that at least that duration of the therapy will be applied per therapy period (e.g. at least 8 hours of therapy per day). The delivered therapy can be intermittent or continuous. Some scheduler embodiments use parameter(s) to control intermittent stimulation during the therapy period, such as duty cycle or stimulation period. The duty cycle represents the percentage of time during which stimulation is delivered for a stimulation period. A therapy period (e.g. on the order of a day) can include many stimulation periods (e.g. less than five minutes or on the order of one minute). The scheduler parameters can include start and stop parameters, start and duration parameters, or other parameters that can be used to control the schedule of neural stimulation. Some of the parameter examples can be derived from others (e.g. start and stop times can be derived from start and duration). The illustrated controller also includes a module to control neural stimulation intensity 1530. Therapy inputs and/or therapy feedback can be used to appropriately adjust one or more stimulation parameter(s) to increase, decrease or maintain a desired neural stimulation intensity. For example, the amplitude, frequency, and/or pulse width of a neural stimulation pulse train can be adjusted to titrate the neural stimulation intensity. Some embodiments adjust the neural stimulation schedule to adjust the neural stimulation intensity. Examples of schedule parameters include therapy duration, start/stop times, stimulation period, stimulation train duration per stimulation period, and duty cycle. For embodiments that allow some schedule parameters to be modified, the scheduler limits the extent of any allowed modifications to the schedule parameters. For example, the duty cycle of the stimulation can be adjusted to a value less than or equal to the maximum duty cycle (e.g. 50%) permitted by the scheduler or within a range of duty cycles permitted by the scheduler. In another example, the therapy duration can be adjusted to a value greater than or equal to the minimum value (e.g. 8 hours per day) for the duration of the therapy permitted by the controller.

Figure 17:
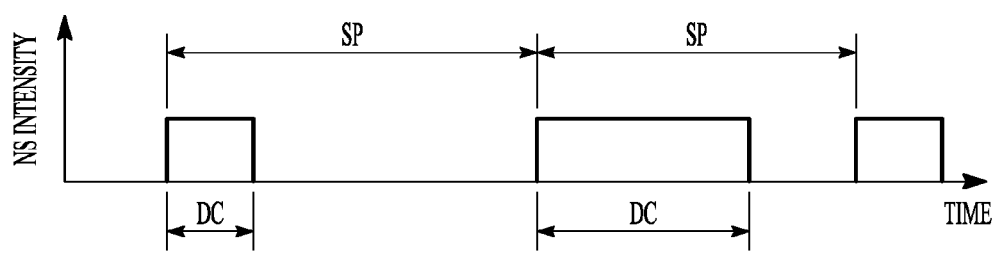
FIG. 17 illustrates intermittent stimulation with variable stimulation periods (SP) and duty cycles (DC).
Figure 18:
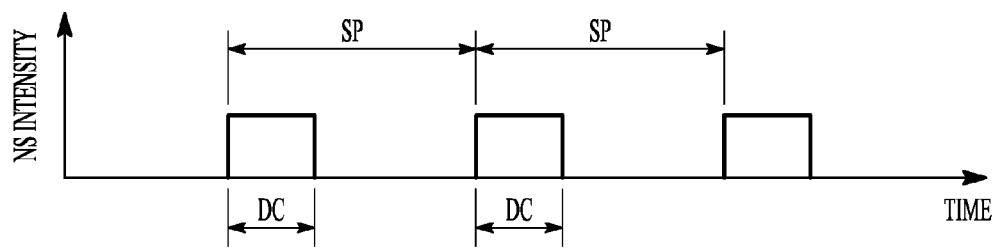
FIG. 18 illustrates intermittent stimulation with constant stimulation periods (SP) and duty cycles (DC).

Various embodiments of the present subject matter deliver intermittent neural stimulation. For example, intermittent neural stimulation may be delivered to treat chronic diseases such as heart failure and hypertension. Some of the terms used to discuss intermittent stimulation are illustrated in FIGS. 17 and 18. Intermittent neural stimulation can be delivered using a duty cycle of a stimulation period. FIGS. 17 and 18 plot neural stimulation intensity against time. FIG. 17 illustrates intermittent stimulation with variable stimulation periods (SP) and duty cycles (DC), and FIG. 18 illustrates intermittent stimulation with constant stimulation periods (SP) and duty cycles (DC). Each duty cycle can include a train of neural stimulation pulses. The duty cycle and stimulation period need not be constant throughout the therapy. For example, the duration or frequency of the duty cycle can be adjusted to adjust an intensity of the therapy. Also, the start and/or stop of the duty cycle can be dependent on enabling conditions. The duty cycle and/or stimulation period can be adjusted in every subsequent stimulation period. Unless expressly disclosed otherwise herein, "stimulation period" and "duty cycle" are not intended to only encompass constant values that result in neural stimulation in a precise periodic manner (e.g. FIG. 18), but rather is intended to include intermittent neural stimulation where therapeutically-effective or prophylactically-effective neural stimulation is delivered for a time and then not delivered for a time, and then delivered for a time (e.g. FIG. 17). In electrical stimulation, for example, a train of neural stimulation pulses (current or voltage) can be delivered during a duty cycle of stimulation. Stimulation waveforms can be square pulses or other shapes. The stimulation pulses can be monophasic or biphasic pulses.

One of ordinary skill in the art will understand that, the modules and other circuitry shown and described herein can be implemented using software, hardware, firmware and combinations thereof. As such, the terms module and circuitry, for example, are intended to encompass software implementations, hardware implementations, firmware implementations, and combinations thereof.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system, comprising:
a posture change detector configured to detect posture transitions including a posture change determined to be indicative of an increased risk of syncope; and
a neural stimulator configured to deliver a scheduled neural stimulation therapy, the neural stimulator including a syncope avoidance module configured to temporarily override the scheduled neural stimulation therapy to ameliorate the risk of increased syncope only in response to detecting the posture change that is determined to be indicative of the increased risk of syncope, and then return to the scheduled neural stimulation therapy after the risk of syncope from the detected posture change has subsided.

2. The system of claim 1, wherein the posture change detector comprises a posture monitor including:
an activity sensor configured to sense patient activity;
an activity sampler configured to control the activity sensor to sample patient activity and detect an increase in patient activity;
a posture sensor configured to sense patient posture; and
a posture sampler configured to control the posture sensor, in response to a detected increase in patient activity, to sample patient posture.

3. The system of claim 1, wherein the posture change detector includes an accelerometer.

4. The system of claim 3, wherein the posture change detector includes a 3-axis accelerometer.

5. The system of claim 1, wherein the posture change detector includes:
a posture monitor configured to monitor posture; and
a posture analyzer configured to detect a significant change in the monitored posture, the significant change determined to be the posture change indicative of the increased risk of syncope.

6. The system of claim 5, wherein the posture monitor includes at least one posture sensor configured to sense a patient posture, and a posture sampler configured to sample the sensed patient posture.

7. The system of claim 5, wherein the posture analyzer is configured to detect a posture change greater than a threshold.

8. The system of claim 7, wherein the posture analyzer is further configured to detect a rate of posture change.

9. The system of claim 5, wherein the posture analyzer is configured to sense at least two posture states, and detect at least one posture state change.

10. The system of claim 5, wherein the posture analyzer is configured to determine if the posture change is a change toward a more upright state or a change toward a more reclined state.

11. The system of claim 5, wherein the posture analyzer is configured to receive a contextual input, and use the contextual input to determine if a posture change is a significant posture change, wherein the contextual input includes at least one input selected from the group of inputs consisting of: a current posture state; at least one sensed physiological parameter; a clock; and a circadian rhythm input.

12. The system of claim 5, wherein:
the posture monitor includes at least two sensors selected from the group of sensors consisting of: a posture sensor; an activity sensor; and an accelerometer; and
the posture analyzer is configured to detect the significant change in the monitored posture that increases the risk of syncope using the at least two sensors.

13. The system of claim 1, wherein the neural stimulator is configured to temporarily adjust an autonomic nervous system (ANS) stimulation to reduce parasympathetic activity or increase sympathetic activity in response to detecting the posture change, allowing increased blood pressure to rise to ameliorate the risk of increased syncope.

14. The system of claim 1, wherein the neural stimulator is configured to deliver a chronic baroreflex stimulation therapy, the chronic baroreflex stimulation therapy including intermittent stimulation of alternating stimulation ON and stimulation OFF periods, each stimulation ON period including a train of neural stimulation pulses.

15. The system of claim 14, wherein the chronic baroreflex stimulation therapy includes a hypertension therapy or a heart failure therapy.

16. The system of claim 14, wherein the syncope avoidance module is configured to respond to the detected posture transition by preventing the intermittent stimulation from initiating the train of stimulation pulses for a time after the detected posture transition.

17. A method implemented using a system that includes a posture change detector configured to detect posture transitions including a posture change determined to be indicative of an increased risk of syncope and a neural stimulator that includes a syncope avoidance module, the method comprising:
   delivering a scheduled neural stimulation therapy using the neural stimulator;
   detecting the posture change, using the posture change detector, determined to be indicative of the increased risk of syncope; and
   temporarily overriding the scheduled neural stimulation therapy, using the syncope avoidance module, only in response to detecting the posture change determined to be indicative of the increased risk of syncope to ameliorate the risk of increased syncope, and then returning to the scheduled neural stimulation therapy after the risk of syncope from the detected posture change has subsided.

18. The method of claim 17, wherein temporarily overriding the scheduled neural stimulation therapy includes temporarily an autonomic nervous system (ANS) stimulation to reduce parasympathetic activity or increase sympathetic activity, allowing increased blood pressure to rise to ameliorate the risk of increased syncope.

19. The method of claim 17, wherein:
   delivering the neural stimulation therapy includes delivering a chronic baroreflex stimulation therapy with intermittent stimulation of alternating stimulation ON and stimulation OFF periods, each stimulation ON period including a train of neural stimulation pulses; and
   temporarily overriding the neural stimulation therapy includes preventing initiation of the train of stimulation pulses for a time after the detected posture transition.

20. The method of claim 17, wherein detecting the posture transition includes:
   sampling patient activity using an activity sensor configured to sense patient activity and detect an increase in patient activity; and
   sampling patient posture in response to a detected increase in patient activity using a posture sensor configured to sense patient posture.

\* \* \* \* \*